United States Patent [19]
Holt et al.

[11] Patent Number: 5,840,552
[45] Date of Patent: Nov. 24, 1998

[54] PREPARATION OF PHARMACEUTICALLY ACTIVE COMPOUNDS BY BIOOXIDATION

[75] Inventors: Robert Holt, Fleetham, United Kingdom; Per Lindberg, Mölndal, Sweden; Christopher Reeve, Middlesborough; Stephen Taylor, Darlington, both of United Kingdom

[73] Assignee: Astra Aktiebolag, Sodertalje, Sweden

[21] Appl. No.: 569,114

[22] PCT Filed: Nov. 27, 1995

[86] PCT No.: PCT/SE95/01415

§ 371 Date: Nov. 21, 1996

§ 102(e) Date: Nov. 21, 1996

[87] PCT Pub. No.: WO96/17076

PCT Pub. Date: Jun. 6, 1996

[30] Foreign Application Priority Data

Nov. 28, 1994 [GB] United Kingdom .................... 9423970

[51] Int. Cl.⁶ ...................................................... C12P 17/16
[52] U.S. Cl. .......................................... 435/118; 546/273.3
[58] Field of Search .......................... 546/273.3; 435/118

[56] References Cited

U.S. PATENT DOCUMENTS 5,049,674 9/1991 Brandstrom et al. ................. 546/273.3
5,430,042 7/1995 Lindberg et al. ........................ 514/338

FOREIGN PATENT DOCUMENTS 4035455 5/1992 Germany .
9617076 11/1995 WIPO .

OTHER PUBLICATIONS

Cashman, J.R. et al. 1993 "Chemical, enzymatic and Human enditioselective S–oxygenation" Durg Metabolism and Disposition vol. 21.

*Primary Examiner*—Jane Fan
*Attorney, Agent, or Firm*—White & Case L.L.P.

[57] ABSTRACT

Enantiomeric or enantiomerically enriched $H^+K^+ATPase$ inhibiting pyridinylsulfinyl—benzimidazoles are prepared using microorganisms or microbial enzyme systems to enantioselectively biooxidize corresponding prochiral sulfide compounds and isolating the pharmaceutically active enantiomer or enantiomerically enriched sulfoxide form.

9 Claims, No Drawings

PREPARATION OF PHARMACEUTICALLY ACTIVE COMPOUNDS BY BIOOXIDATION

The present invention relates to a method of preparing compounds as defined below, either as a single enantiomer or in an enantiomerically enriched form, by biooxidation of their sulphide equivalents.

BACKGROUND TO THE INVENTION

The racemic form of the compounds prepared by the method of the present invention are known compounds. Some of the compounds are also known in single enantiomeric form. The compounds are active $H^+K^+ATPase$ inhibitors and they, including their pharmaceutically acceptable salts, are effective acid secretion inhibitors, and known for use as antiulcer agents. The compounds, which include the known compounds omeprazole (compound of formula (IIa) below), lansoprazole (compound of formula (IIc) below) and pantoprazole (compound of formula (IIb) below), are known for example from European Patent Specifications EP 5129 and 124495, EP 174726 and EP 166287.

These compounds, being sulfoxides, have an asymmetric centre in the sulfur atom, i.e. exist as two optical isomers (enantiomers). It is desirable to obtain compounds with improved pharmacokinetic and metabolic properties which will give an improved therapeutic profile such as a lower degree of interindividual variation.

The separation of enantiomers of omeprazole in analytical scale is described in e.g. J. Chromatography, 532 (1990), 305–19. Also the separation of enantiomers of compounds, including omeprazole and pantoprazole, is described in German Patent Specification DE 4035455.

Recently there has been a great deal of literature published relating to the synthesis of optically active compounds using biocatalysts. The majority of this work has been aimed at finding routes to single enantiomer forms of pharmaceuticals. The reactions receiving most attention have been those involved in the preparation of esters, acids and alcohols due to the general utility of these functionalities in synthesis and also because the biocatalysts are readily available.

Studies on the synthesis of optically active sulfoxides are relatively rare partly due to the small number of pharmaceuticals containing sulfoxide groups and partly due to the fact that enzymes that react with the sulphur centre are not available commercially. The synthesis of optically active sulfoxides has been described in Holland, H. L. (1988) Chem. Rev. 88, 473–483 and Phillips, R. S. and Sheldon W. M., Enzyme Microb. Technol., 1981, Vol. 3, January, 9–18.

DESCRIPTION OF THE INVENTION

According to the present invention there is provided a method of preparing a compound of formula (II) either as a single enantiomer or in an enantiomerically enriched form:

wherein
$Het_1$ is

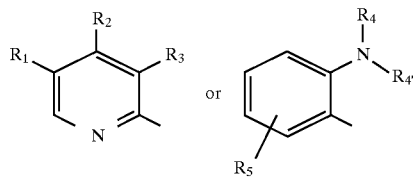

and
$Het_2$ is

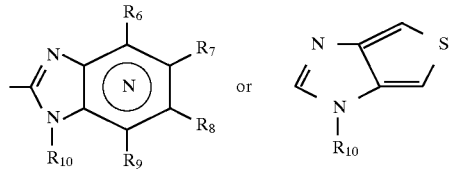

and
X is

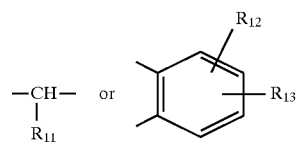

wherein:
N in the benzimidazole moiety means that one of the carbon atoms substituted by $R_6-R_9$ optionally may be exchanged for an unsubstituted nitrogen atom;
$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenylalkyl, phenylalkoxy;
$R_4$ and $R_{4'}$ are the same or different and selected from hydrogen, alkyl, aralkyl;
$R_5$ is hydrogen, halogen, trifluoromethyl, alkyl, alkoxy;
$R_6-R_9$ are the same or different and selected from hydrogen, alkyl, alkoxy, halogen, haloalkoxy, alkylcarbonyl, alkoxycarbonyl, oxazolyl, trifluoroalkyl or adjacent groups $R_6-R_9$ may complete together with the carbon atoms to which they are attached optionally substituted ring structures;
$R_{10}$ is hydrogen or alkoxycarbonyloxymethyl;
$R_{11}$ is hydrogen or forms an alkylene chain together with $R_3$;
$R_{12}$ and $R_{13}$ are the same or different and selected from hydrogen, halogen or alkyl, which method comprises stereoselective biooxidation of the pro-chiral sulfide counterpart compound.

The compounds of formula (II) are active $H^+K^+ATPase$ inhibitors. By the method of the invention these compounds, which are sulfoxides, are obtained in single enantiomer form or such that one enantiomeric form is present in excess leading to an optically active product, by stereoselective biooxidation of the pro-chiral starting sulfide counterpart compound.

In the above definitions alkyl groups or moieties may be branched or straight chained or comprise cyclic alkyl groups, for example cycloalkylalkyl.

Preferably:

Het₁ is

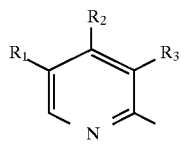

and

Het₂ is

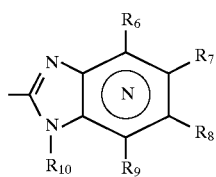

and

(wherein $R_1$, $R_2$, $R_3$, $R_6$ to $R_9$, $R_{10}$ and $R_{11}$ are as defined above).

Most preferably the compounds of formula (II) are compounds of the formula (IIa) to (IIe):

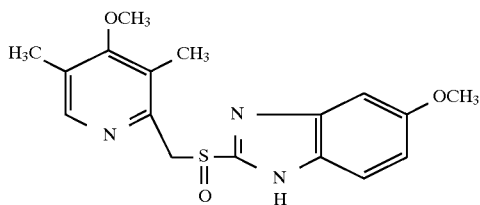 (IIa)

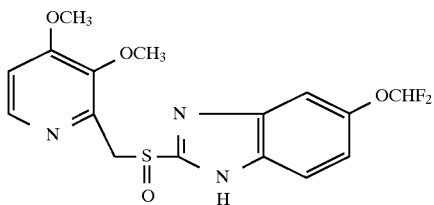 (IIb)

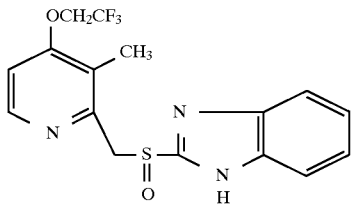 (IIc)

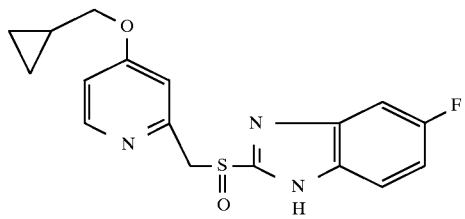 (IId)

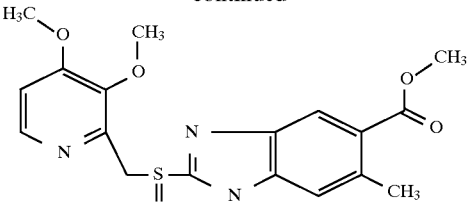 (IIe)

An example of a compound of formula (II) wherein $R_{10}$ is alkoxycarbonyloxymethyl is

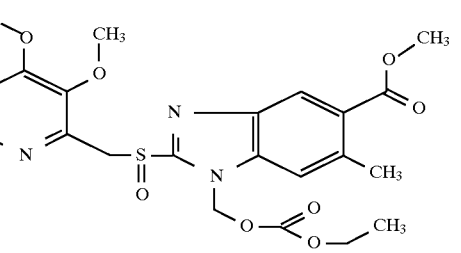 (IIf)

The starting prochiral sulfides used in the method of the present invention are of the formula:

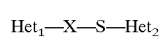 (I)

wherein Het₁, X and Het₂ are as defined above.

In order to obtain each of the above compounds (IIa)–(IIf), the following starting compounds of formula (Ia) to (If), respectively will be required:

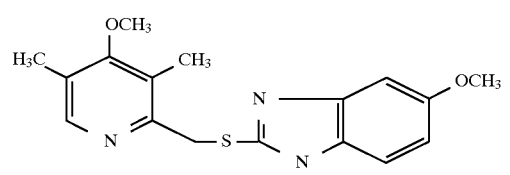 (Ia)

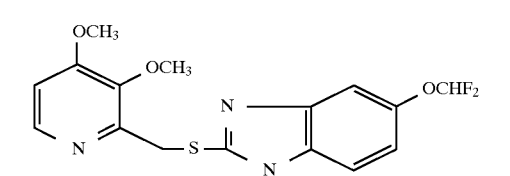 (Ib)

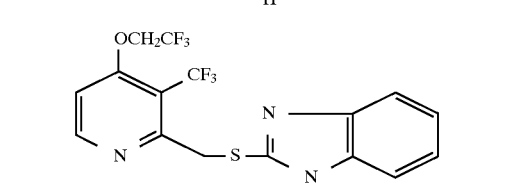 (Ic)

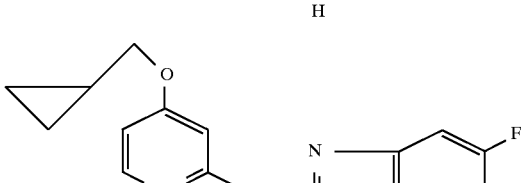 (Id)

-continued

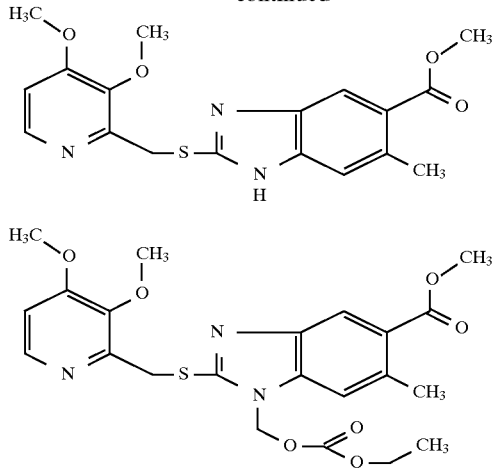

The compounds prepared by the method of the invention possess a stereogenic (asymmetric) centre which is the sulfur atom which forms the sulfoxide group between the Het$_1$—X-moiety and the Het$_2$-moiety.

The stereoselective biooxidation according to the present invention may be carried out using a microorganism or an enzyme system derivable therefrom. Suitable microorganisms may be selected from alkane oxidisers including *Arthrobacter petroleophagus, Brevibacterium paraffinolyticum,* and Acinetobacter species, alkene oxidisers such as Mycobacterium species, and a variety of fungal species particularly Penicillium species (*Penicillium frequentans*).

According to one embodiment of the invention the method comprises contacting the pro-chiral sulfide counterpart compound with a microorganism which is
*Penicillium frequentans*
*Rhizopus stolonifer*
*Cunninghamella elegans*
*Ustilago maydis*
*Arthrobacter petroleophagus*
*Brevibacterium paraffinolyticum*
Acinetobacter sp.
Mycobacterium sp.
or *Aspergillus niger*
Preferably the microorganism is:
*Penicillium frequentans* BPFC 386, 585, 623, 733
*Rhizopus stolonifer* BPFC 1581
*Ustilago maydis* BPFC 1198, 6333
*Arthrobacter petroleophagus* ATCC 21494
*Brevibacterium paraffinolyticum* ATCC 21195
Actinetobacter Sp. NCIMB 9871
Mycobacterium sp. BPCC 1174, 1178, 1179, 1186, 1187
or *Aspergillus niger* BPFC 32

The microorganisms may be grown on suitable medium containing an appropriate carbon source such as octane, ethene, cyclohexanone or glucose for example.

The compounds of formula (II) are generally acid labile and thus the use of acid conditions is to be avoided. Generally the method according to the invention may be carried out at a pH of 7.6 to 8, suitably about 7.6, and at temperature of 25°–35° C., suitably about 28° C.

The present invention will now be illustrated with reference to the Examples.

EXAMPLE 1

The following microorganisms were screened for sulfoxidation activity against compounds of formula (Ia):

*Penicillium frequentans* BPFC 386
*Penicillium frequentans* BPFC 585
*Penicillium frequentans* BPFC 623
*Penicillium frequentans* BPFC 733
*Rhizopus stolonifer* BPFC 1581
*Ustilago maydis* BPFC 1198
*Ustilago maydis* BPFC 6333
*Arthrobacter petroleophagus* ATCC 21494
*Brevibacterium paraffinolyticum* ATCC 21195
Acinetobacter sp NCIMB 9871
Mycobacterium sp BPCC 1174
Mycobacterium sp BPCC 1178
Mycobacterium sp BPCC 1179
Mycobacterium sp BPCC 1186
Mycobacterium sp BPCC 1187

Growth Conditions

The growth conditions for the above microorganisms were as follows. The following fungi:
*Penicillium frequentans* BPFC 386
*Penicillium frequentans* BPFC 585
*Penicillium frequentans* BPFC 623
*Penicillium frequentans* BPFC 733
*Rhizopus stolonifer* BPFC 1581
*Ustilago maydis* BPFC 1198
*Ustilago maydis* BPFC 6333
were grown in 200 ml of sterile liquid medium (I) with the composition of (per liter) $K_2HPO_4$ (1.9 g), $NaH_2PO_4 2H_2O$ (2.02 g), ammonium sulfate (1.8 g), magnesium sulfate (0.2 g), ferric chloride (0.97 mg), and trace elements solution (1 ml) pH 7.2. The composition of the trace elements solution used was as follows (in g/l):

| | |
|---|---|
| $CuSO_4.5H_2O$ | 0.02 |
| $MnSO_4.4H_2O$ | 0.1 |
| $ZnSO_4.7H_2O$ | 0.1 |
| $CaCO_3$ | 1.8 |

The above medium was supplemented with 0.2% w/v yeast extract and 2.2% w/v glucose. The medium contained in 1L baffled flasks was inoculated either by adding a suspension of spores in sterile distilled water or by the addition of a plug of agar containing the fungi from a Sabouraud Dextrose plate. Fungi were grown at 28° C. on a rotary shaker at 150 rpm for 48 hours. With the exception of *Ustilago maydis*, the fungal biomass obtained from liquid culture was harvested by filtration on a Whatman Grade 113 filter paper and washed on the filter with 50 mM sodium phosphate buffer, pH7.6. *Ustilago maydis* was harvested by centrifuging for 20 minutes at 8,000 rpm and 4° C. The biomass was washed by resuspending in 50 mM sodium phosphate buffer, pH 7.6 and centrifuging as above.

The bacteria were grown with the sources of carbon shown in Table 1:

TABLE 1

| Microorganism | Carbon Source |
|---|---|
| *Arthrobacter petroleophagus* ATCC 21494 | Octane |
| *Brevibacterium paraffinolyticum* ATCC 21195 | Octane |
| *Acinetobacter sp* NCIMB 9871 | Cyclohexanone |
| *Mycobacterium sp* BPCC 1174, 1178, 1179, 1186, 1187 | Ethene |

The growth of Acinetobacter sp. NCIMB 9871 on cyclohexanone was performed in 100 ml of liquid medium (I) in a 500 ml baffled flask containing a centre well. Cydohexanone was placed in the centre well. The microorganism was grown at 28° C. on a rotary shaker at 150 rpm for 24–48 hours.

Growth of *Arthrobacter petroleophagus* ATCC 21494 and *Brevibacterium paraffinolyticum* ATCC 21195 on octane was performed in 200 ml of liquid medium (I) containing 0.2% w/v yeast extract in a 1L baffled flask. Octane (1 ml) was added directly to the medium without sterilization. The above microorganisms were grown at 28° C. on a rotary shaker at 150 rpm for 24–48 hours.

Mycobacterium sp BPCC 1174, 1178, 1179, 1186 and 1187 were grown in 500 ml liquid medium (I) in a 2L non-baffled flask fitted with a rubber bung. The flask was partially evacuated and then charged with ethene. Growth was conducted at 28° C. on a rotary shaker at 150 rpm for 7 days.

Growth of *Arthrobacter petroleophagus* ATCC 21494 and *Brevibacterium paraffinolyticum* ATCC 21195 was also performed on glucose. Each microorganism was inoculated into 200 ml medium (I) containing 0.2% w/v yeast extract and 2.2% w/v glucose. Growth was performed at 28° C. on a rotary shaker at 150 rpm for 24–48 hours.

All bacteria were harvested from liquid medium by centrifuging at 8,000 rpm and 4° C. for 20 minutes. Cells were washed by resuspending in 50 mM sodium phosphate buffer, pH 7.6 followed by centrifuging as above.

Biooxidation Reactions

Biotransformations were performed for each microorganism in 50 mM sodium phosphate buffer, pH 7.6 with 5–10 g/l dry cell weight and a substrate concentration of 1 g/l. The cells were incubated with the compound of formula (Ia) on a rotary shaker at 28° C. for 18–20 hours.

Samples were removed from the biotransformation and either centrifuged or filtered to remove biomass and analysed directly.

Detection of Products

The biooxidation of the compound of formula (Ia) was followed by reverse phase HPLC on a Spherisorb S5-ODS2 reverse phase column eluted with a 50:50 mixture of acetonitrile and 25 mM sodium phosphate buffer, pH 7.6 at a flow rate of 0.8 ml/min. Under such conditions the compounds of formulae (IIa) and (Ia) were well resolved with retention times of 5.2 and 9.8 minutes respectively. Both compounds were detected at a wavelength of 300 nm.

The enantiomeric composition of the compound of formula (IIa) formed was investigated by the following method. After removal of biomass the aqueous media was extracted with two volumes of ammonia saturated dichloromethane. The pooled organic extracts were dried over anhydrous sodium sulfate and the solvent was evaporated under reduced pressure to afford a pale brown solid. Then the enantiomeric composition of sulfoxide was determined by chiral HPLC on a Chiralpak AD Column under the following conditions:

Column Chiralpack AD 250 mm×4.6 mm interior diameter with 50 mm guard column

Eluent Hexane:Ethanol:Methanol (40:55:5% V/V)

Flow 1.0 ml/min

Injection Volume 20 µl

Wavelength 300 nm

Retention times

Compound of formula (Ia) 5.1 min

Compound of formula (IIa):

(+) Enantiomer 8.5 min (−) Enantiomer 13.4 min

The following results were obtained:

TABLE 2

| Microorganism | Compound of Formula (IIa) (ppm) | Enantiomeric excess (%) | Enantiomer ((+) or (−)) |
|---|---|---|---|
| *Penicillium frequentans* BPFC 386 | 23 | >99 | (−) |
| *Penicillium frequentans* BPFC 585 | 2.1 | >99 | (−) |
| *Penicillium frequentans* BPFC 623 | 3.0 | 95 | (−) |
| *Penicillium frequentans* BPFC 733 | 2.6 | 87 | (−) |
| *Rhizopus stolonifer* BPFC 1581 | 3.0 | 56 | (−) |
| *Ustilago maydis* BPFC 1198 | 8.0 | 88 | (−) |
| *Ustilago maydis* BPFC 8333 | 34.0 | 99 | (−) |
| *Arthrobacter petroleophagus* ATCC 21494 | 24.0 | 96 | (−) |
| *Brevibacterium paraffinolyticum* ATCC 21195 | 13.0 | >99 | (−) |
| *Acinetobacter sp* NCIMB 9871 | 0.4 | 17 | (−) |
| *Mycobacterium sp* BPCC 1174 | 10.0 | 97 | (−) |
| *Mycobacterium sp* BPCC 1178 | 3.3 | 93 | (−) |
| *Mycobacterium sp* BPCC 1179 | 9.0 | 96 | (−) |
| *Mycobacterium sp* BPCC 1186 | 11.0 | 97 | (−) |
| *Mycobacterium sp* BPCC 1187 | 6.0 | 96 | (−) |

The enantiomeric excess value gives an indication of the relative amounts of each enantiomer obtained. The value is the difference between the relative percentages for the two enantiomers. Thus, for example, when the percentage of the (−) enantiomer of the formed sulfoxide is 97.5% and the percentage for the (+) enantiomer is 2.5%, the enantiomeric excess for the (−) enantiomer is 95%.

With *Arthrobacter petroleophagus* ATCC 21494 and *Brevibacterium paraffinolyticum* ATCC 21195 the stereoselectivity of the biooxidation was unaffected by the choice of carbon source used for growth (octane and glucose).

EXAMPLE 2

Compounds of formula (Id) and (Ie) were screened against a range of microorganisms for the production of the corresponding sulfoxides. The growth of microorganisms and subsequent biotransformations were performed as in Example 1 except that the reaction times were as listed in Tables 5 and 6. *Aspergillus niger* BPFC 32 was grown in the same way as the fungi were grown in Example 1.

Detection of Products

The biooxidation of the compounds of formula (Id) and (Ie) was followed by reverse phase HPLC as in Example 1 except that the retention times were as follows:

TABLE 3

| Compound of formula | Retention time (min) |
|---|---|
| Id | 13.7 |
| IId | 5.0 |
| Ie | 9.4 |
| IIe | 4.3 |

The enantiomeric composition of the compounds of formula (IId) and (IIe) was investigated by the method of Example 1 except in the chiral HPLC the solvent compositions, flow rates and retention times were as follows:

TABLE 4

| Compound of formula | Solvent Composition | Flow rate (ml/min) | Retention Time |
|---|---|---|---|
| IId | Hexane/Ethanol (70:30% v/v) | 1.0 | 12.9 (Enantiomer A) 21.7 (Enantiomer B) |
|  | Hexane/Ethanol/Methanol (40.55:5% v/v) | 1.0 | 7.4 (Enantiomer A) 10.6 (Enantiomer B) |
| IIe | Hexane/Ethanol (70:30% v/v) | 1.0 | 26.0 (Enantiomer A) 30.5 (Enantiomer B) |

In Table 4 the first enantiomer eluted is referred to as enantiomer A and second as enantiomer B. The results are summarised in Tables 5 and 6.

TABLE 5

| Microorganism | Reaction time (h) | Aqueous concentration (PPM) Compound of formula (Id) | Aqueous concentration (PPM) Compound of formula (IId) | E.e. % | Enantiomer |
|---|---|---|---|---|---|
| *Mycobacterium sp.* BPCC 1174 | 42 | 5 | 16.7 | >99 | A |
| *Mycobacterium sp.* BPCC 1178 | 42 | 5.9 | 14.4 | >99 | A |
| *Mycobacterium sp.* BPCC 1179 | 42 | 6.6 | 17.4 | >99 | A |
| *Mycobacterium sp.* BPCC 1186 | 42 | 4.8 | 42 | >99 | A |
| *Mycobacterium sp.* BPCC 1187 | 42 | 7.4 | 18.3 | >99 | A |
| *Arthrobacter petroleophagus* ATCC 21494 | 42 | 3.5 | 6.6 | >99 | A |
| *Brevibacterium paraffinolyticum* ATCC 21195 | 42 | 2.6 | 21.7 | >99 | A |
| *Ustilago maydis* BPFC 1198 | 18 | 6.7 | 45 | >99 | A |
| *Ustilago maydis* BPFC 6333 | 18 | 4.6 | 43 | >99 | A |
| *Aspergillus niger* BPFC 32 | 42 | 5.6 | 2.7 | — | — |
| *Penicillium frequentans* BPFC 386 | 18 | 5 | 0 | — | — |
| *Penicillium frequentans* BPFC 585 | 48 | 5.2 | 0 | — | — |
| *Penicillium frequentans* BPFC 623 | 48 | 4.5 | 0 | — | — |
| *Penicillium frequentans* BPFC 733 | 18 | 3.5 | 0 | — | — |

(E.e. means Enantiomeric excess)

TABLE 6

| Microorganism | Reaction time (h) | Aqueous concentration (PPM) Compound of formula (Ie) | Aqueous concentration (PPM) Compound of formula (IIe) | E.e. (%) | Enantiomer |
|---|---|---|---|---|---|
| *Mycobacterium sp.* BPCC 1179 | 42 | 1.6 | 3.3 | >99 | A |
| *Arthrobacter petroleophagus* ATCC 21494 | 42 | 3.2 | 0 | — | — |
| *Brevibacterium paraffinolyticum* ATCC 21195 | 72 | 4.0 | 1.6 | — | — |
| *Ustilago maydis* BPFC 1198 | 18 | 2.3 | 0 | — | — |
| *Ustilago maydis* BPFC 6333 | 72 | 3.2 | 0 | — | — |
| *Asergillus niger* BPFC 32 | 72 | 3.7 | 9.2 | — | — |
| *Penicillium frequentans* BPFC 386 | 72 | 3.1 | 0.5 | — | — |
| *Penicillium frequentans* BPFC 585 | 48 | 3.2 | 3.2 | — | — |
| *Penicillium frequentans* BPFC 623 | 48 | 2.9 | 1.5 | 83.4– | B |
| *Penicillium frequentans* BPFC 733 | 18 | 3.2 | 0 | — | — |

The oxidation of the compound of formula (Id) produced in all cases the "A" enantiomer of the compound of formula (IId) in excellent enantiomeric excess but in low yield. The four strains of *Penicillium frequentans* previously shown to oxidise the compound of formula (Ia), failed to oxidise the compound of formula (Id).

The oxidation of the compound of formula (Ie) produced fewer results. This compound proved to be particularly insoluble making the detection of product difficult. Whilst in a number of cases sulfoxide was produced, its concentration was too low to determine the enantiomeric excess. However two results were obtained with Mycobacterium sp. and *Penicillium frequentans* both affording sulfoxide of high enantiomeric excess but interestingly of opposite stereoselectivity.

EXAMPLE 3

The microorganisms listed in Table 9 below were screened for sulfoxidation activity against compounds of formula (Ib). They were grown under the same condition as in Examples 1 and 2.

Biotransformations were performed following the protocol of Example 1 except that the dry cell weight was increased to approximately 20 $gL^{-1}$ and the reaction time was extended.

Detection of Products

The biooxidation of the compound of formula (Ib) was followed by reverse phase HPLC as in Example 1 except that the retention times were as follows:

TABLE 7

| Compound of formula | Retention time (min) |
|---|---|
| Ib | 8.1 |
| IIb | 4.2 |

The enantiomeric composition of the compound of formula (IIb) was investigated by the method of Example 1 except in the chiral HPLC the solvent composition, flow rate and retention time were as follows:

TABLE 8

| Solvent composition | Flow Rate (ml/min) | Retention times (min) |
|---|---|---|
| Hexane/ethanol (70:30%) | 1.0 | 32.3 (Enantiomer A) |
| | | 36.6 (Enantiomer B) |

In Table 8 the first enantiomer eluted is referred to as enantiomer A and the second as enantiomer B.

The results are summarised in the following table:

TABLE 9

| Microorganism | Reaction time (h) | Compound of formula (Ib) | Compound of formula (IIb) | E.e. % | Enantiomer |
|---|---|---|---|---|---|
| *Mycobacterium sp.* BPCC 1178 | 72 | 8.6 | 3.4 | 8.2 | B |
| *Brevibacterium paraffinolyticum* ATCC 21195 | 72 | 8.4 | 4.0 | 26.6 | B |
| *Ustilago maydis* BPFC 6333 | 72 | 8.2 | 4.3 | >99 | A |
| *Aspergillus niger* BPFC 32 | 72 | 5.6 | 28.0 | >99 | A |
| *Penicillium frequentans* BPFC 386 | 72 | 8.4 | 4.5 | — | — |
| *Penicillium frequentans* BPFC 585 | 48 | 6.5 | 11.4 | — | — |
| *Penicillium frequentans* BPFC 623 | 48 | 7.7 | 6.5 | — | — |

(E.e. means enantiomeric excess)

The microorganisms listed in Table 9 were also screened under identical conditions for sulfoxidation of the compound of formula (Ic) but no product of formula (IIc) could be detected.

Deposits Of Microorganisms

The following microorganisms were deposited at the National Collections of Industrial and Marine Bacteria Ltd (NCIMB), 23 St. Machar Drive, Aberdeen, Scotland AB2 1RY on 25 Nov. 1994:

1. *Mycobacterium sp* BPCC 1174 Accession No. NCIMB 40695
2. *Mycobacterium sp* BPCC 1178 Accession No. NCIMB 40696
3. *Mycobacterium sp* BPCC 1179 Accession No. NCIMB 40697
4. *Mycobacterium sp* BPCC 1186 Accession No. NCIMB 40698
5. *Mycobacterium sp* BPCC 1187 Accession No. NCIMB 40699

The following microorganisms were deposited at the International Mycological Institute (IMI), Bakeham Lane, Englefield Green, Egham, Surrey TW20 9TY, England on 28 Nov. 1994:

6. *Penicillium frequentans* BPFC 386 Accession No. IMICC 364802
7. *Penicillium frequentans* BPFC 585 Accession No. IMICC 364801
8. *Penicillium frequentans* BPFC 623 Accession No. IMICC 364800
9. *Penicillium frequentans* BPFC 733 Accession No. IMICC 364799
10. *Rhizopus stolonifer* BPFC 1581 Accession No. IMICC 364798
11. *Ustilago maydis* BPFC 1198 Accession No. IMICC 364797
12. *Ustilago maydis* BPFC 6333 Accession No. IMICC 364796
13. *Asperigillus niger* BPFC 32 Accession No. IMICC 364795

We claim:

1. A method of preparing a pharmaceutically active compound as a single sulfoxide enantiomer or an enantiomerically enriched form having the formula (II)

wherein $Het_1$ is

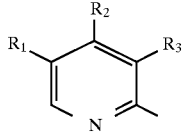

and $Het_2$ is

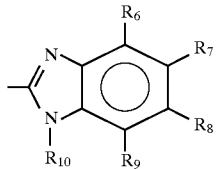

and

X is

$R_1$, $R_2$ and $R_3$ are the same or different and selected from the group consisting of hydrogen, alkyl, alkoxy which is unsubstituted or substituted by fluorine, alkylthio, alkoxyalkoxy, dialkylamino, piperidino, morpholino, halogen, phenylalkyl, and phenylalkoxy;

$R_6$–$R_9$ are the same or different and selected from the group consisting of hydrogen, alkyl, alkoxy, halogen, haloalkoxy, alkylcarbonyl, alkoxycarbonyl, oxazolyl, and trifluoroalkyl;

or adjacent groups R6–R9 together with the carbon atoms to which they are attached form an unsubstituted or substituted ring;

R10 is hydrogen or alkoxycarbonyloxymethyl;

R11 is hydrogen or forms an alkylene chain together with R3;

which method comprises the steps of: enantioselectively biooxidizing a pro-chiral sulfide compound of the formula (I):

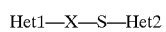

Het1—X—S—Het2 (I)

by means of a microbial organism or a microbial enzyme system; and isolating the pharmaceutically active single enantiomeric or enantiomerically enriched sulfoxide compound.

2. The method according to claim 1 wherein the compound of formula (II) is compound of formula:

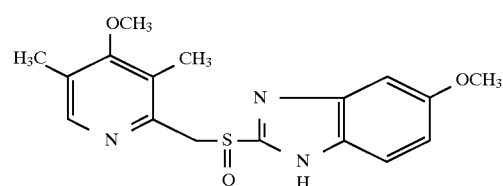

(IIa)

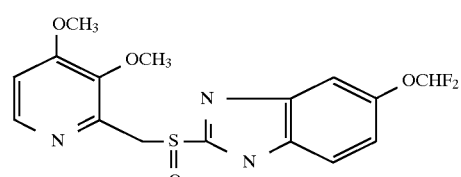

(IIb)

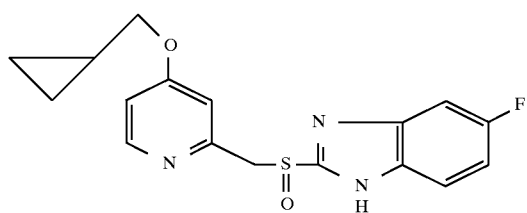

(IId)

or

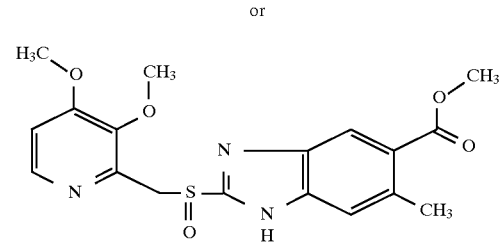

(IIe)

and wherein the compound of formula (I) is a compound of formula:

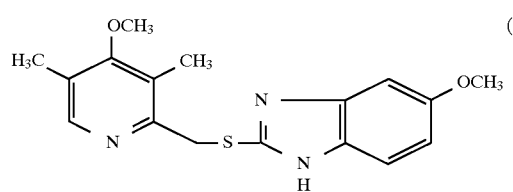

(Ia)

-continued

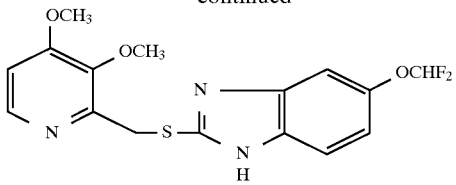

(Ib)

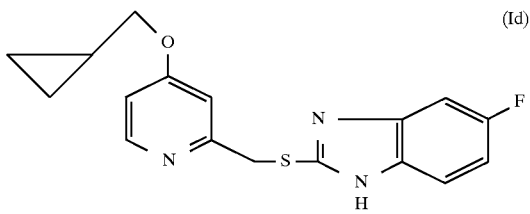

(Id)

or

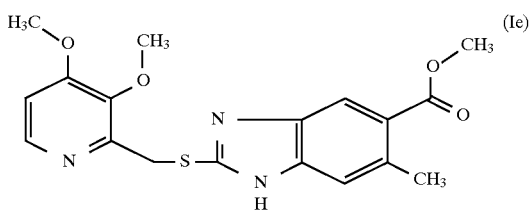

(Ie)

3. A method according to any one of the previous claims wherein a single enantiomer of the compound of formula (II) is prepared.

4. The method according to claim 2, wherein a compound of formula (Ia) is enantioselectively biooxidized to an enantiomeric or enantiomerically enriched sulfoxide of formula (IIa) which is effected by the action of *Penicillium frequentans, Brevibacterium paraffinolyticum,* or Mycobacterium sp.

5. The method according to claim 2, wherein a compound of formula (Ib) is enantioselectively biooxidized to an enantiomeric or enantiomerically enriched sulfoxide of formula (IIb) which is effected by the action of *Aspergillus niger,* or *Ustilago maydis.*

6. The method according to claim 2, wherein a compound of formula (Id) is enantioselectively biooxidized to an enantiomeric or enantiomerically enriched sulfoxide of formula (IId) which is effected by the action of Mycobacterium sp. *Arthrobacter petroleophagus, Brevibacterium paraffinolyticum,* or *Ustilago maydis.*

7. The method according to claim 2, wherein a compound of formula (Ie) is enantioselectively biooxidized to an enantiomeric or enantiomerically enriched sulfoxide of formula (IIe) which is effected by the action of Mycobacterium or *Penicillium frequentans.*

8. A method for the preparation of a pharmaceutically active (−)—enantiomeric sulfoxide compound of formula (IIa) as defined in claim 2, comprising the steps of:

(a) enantioselectively biooxidizing a sulfide form of formula (Ia) as defined using whole cells of *Penicillium frequentans* BPFC 386, *Penicillium frequentans* BPFC 585, *Ustilago maydis* BPFC 6333 or *Brevibacterium parafinolyticum* ATCC 21195; and (b) isolating the pharmaceutically active enantiomeric or enantiomerically enriched sulfoxide compound.

9. A method of preparing a pharmaceutically active compound as a single sulfoxide enantomer or an enantiomerically enriched form of formula (IIa):

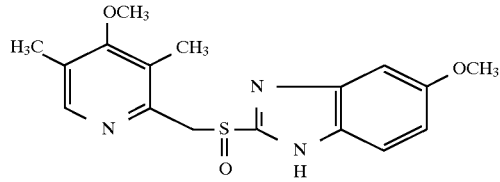

(IIa)

comprising the steps of:

(a) enantioselectively bioxidizing the corresponding prochiral sulfide compound of formula (Ia):

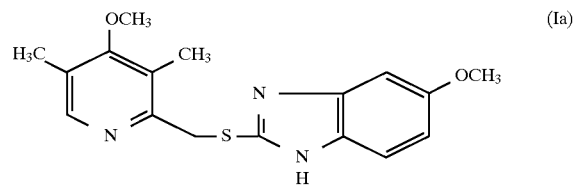

(Ia)

by means of the microbial organism *Ustilago maydis* or a microbial enzyme system isolated therefrom; and (b) isolating the pharmaceutically active single enantiomeric or enantiomerically enriched sulfoxide compound.

* * * * *